United States Patent
Hardy et al.

(10) Patent No.: US 6,826,423 B1
(45) Date of Patent: Nov. 30, 2004

(54) WHOLE BODY STEREOTACTIC LOCALIZATION AND IMMOBILIZATION SYSTEM

(75) Inventors: Tyrone L. Hardy, Del Mar, CA (US); Laura R. Deming, San Diego, CA (US)

(73) Assignee: MIDCO-Medical Instrumentation and Diagnostics Corporation, San Diego, CA (US)

(*) Notice: Subject to any disclaimer, the term of this patent is extended or adjusted under 35 U.S.C. 154(b) by 0 days.

(21) Appl. No.: 10/029,305

(22) Filed: Dec. 20, 2001

Related U.S. Application Data

(63) Continuation-in-part of application No. 09/477,397, filed on Jan. 4, 2000, now abandoned.
(60) Provisional application No. 60/114,942, filed on Jan. 4, 1999.

(51) Int. Cl.⁷ ................................................. A61B 5/05
(52) U.S. Cl. ........................ 600/429; 606/130; 600/426; 600/417; 600/414
(58) Field of Search ................................ 600/407, 411, 600/414, 417, 426, 427, 429, 415; 378/205, 208, 209; 606/130; 5/601

(56) References Cited

U.S. PATENT DOCUMENTS

| | | |
|---|---|---|
| 3,692,023 A | 9/1972 | Phillips et al. |
| 3,783,251 A | 1/1974 | Pavkovich |
| 4,341,220 A | 7/1982 | Perry |
| 4,583,538 A | 4/1986 | Onik et al. |
| 4,608,977 A | 9/1986 | Brown |
| 4,618,978 A | 10/1986 | Cosman |
| 4,638,798 A | 1/1987 | Shelden et al. |
| 4,791,934 A | 12/1988 | Brunnett |
| 4,838,265 A * | 6/1989 | Cosman et al. ................ 606/1 |
| 4,905,267 A * | 2/1990 | Miller et al. ................ 378/208 |
| 5,099,846 A | 3/1992 | Hardy |
| 5,143,076 A | 9/1992 | Hardy et al. |
| 5,176,689 A | 1/1993 | Hardy |
| 5,299,253 A * | 3/1994 | Wessels ...................... 378/163 |
| 5,354,314 A | 10/1994 | Hardy et al. |
| 5,398,684 A | 3/1995 | Hardy |
| 5,442,674 A * | 8/1995 | Picard et al. ................ 378/20 |
| 5,531,229 A | 7/1996 | Dean et al. |
| 5,553,112 A | 9/1996 | Hardy et al. |
| 5,566,681 A | 10/1996 | Manwaring et al. |
| 5,681,326 A * | 10/1997 | Lax ............................ 606/130 |
| 5,682,890 A | 11/1997 | Kormos et al. |
| 5,794,628 A | 8/1998 | Dean |
| 5,908,410 A | 6/1999 | Weber et al. |
| 6,011,828 A | 1/2000 | Hardy et al. |
| 6,143,003 A | 11/2000 | Cosman |
| 6,148,058 A * | 11/2000 | Dobbs ........................ 378/19 |
| 6,533,794 B2 * | 3/2003 | Chakeres .................... 606/130 |

OTHER PUBLICATIONS

Bentel, G.C., Chapter: Treatment Geometry, *Patient Positioning and Immobilization in Radiation Oncology*, McGraw–Hill publishers, pp 1–10 (1999).

(List continued on next page.)

*Primary Examiner*—Eleni Mantis Mercader
(74) *Attorney, Agent, or Firm*—Peacock, Myers & Adams

(57) ABSTRACT

An apparatus and method for aligning and imaging a body part which immobilizes the body part within a stereotactic body localization system having an imaging resolver fiducial localizer for precise imaging and localization of the body parts within the apparatus. Both anterior and posterior immobilization methods can be used. A continuous array of coupled fiducials is employed with at least one pair formed in a $\pi/2$ horizontal linked sine and cosine wave fiducial pattern.

21 Claims, 12 Drawing Sheets

OTHER PUBLICATIONS

Bentel, G.C., Chapter: Treatment Accuracy and Precision, *Patient Positioning and Immobilization in Radiation Oncology*, McGraw–Hill publishers, pp 11–22 (1999).

Bentel, G.C., Chapter: General Consideration of Positioning and Immobilization, *Patient Positioning and Immobilization in Radiation Oncology*, McGraw–Hill publishers, pp 23–37 (1999).

Bentel, G.C., Chapter: Central Nervous System, *Patient Positioning and Immobilization in Radiation Oncology*, McGraw–Hill publishers, pp 71–91 (1999).

Bentel, G.C., et al., Comparison of Two Repositioning Devices Used During Radiation Therapy for Hodgkin's Disease, *Int. J. Radiation Oncology Biol. Phys.*, vol. 38, No. 4, pp. 791–795 (1997).

Bentel, G.C., et al., "Impact of Cradle Immobilization Setup Reproducibility During External Beam Radiation Therapy for Lung Cancer," *Int. J. Radiation Oncology Biol. Phys.*, vol. 38, No. 3, pp 527–531 (1997).

Bertolina, J.A., et al., "Quality Assurance Testing for an Extracranial Stereotactic Device: Methods and Results," Poster No. 129 *Int'l Stereotactic Radiosurgery Society*, p. 233 (1999).

Blomgren, H., et al., "Radiosurgery for Tumors in the Body: Clinical Experience Using a New Method," *Journal of Radiosurgery*, vol. 1, No. 1, pp 63–74 (1998).

Blomgren, H., et al., "Stereotactic High Dose Fraction Radiation Therapy of Extracranial Tumors Using an Accelerator," *Acta Oncologica*, vol. 34, No. 6, pp 861–870 (1995).

Dryzmala, R.E., "Quality Assurance for LINAC–based Stereotactic Radiosurgery,".

MED–TEC, Inc. "UNI–FRAME® Head Immobilization System" Advertisement (1996).

Smithers Medical Products Inc., Product Catalog exclusively featuring: ALPHA CRADLE® Brand Patient Repositioning Systems Advertisement (1995).

Izi Medical Products Corp. World Wide Web Page featuring "Multi–Modality Radiographic Marker" and Multi–Modality Radiographic Markers (Sep. 1999).

Magellan—Biosense ® "Image–Guidance for Brain, Spine and Sinus Surgery," (date unknown).

CIRS Computerized Imaging Reference Systems, Inc. "Dimensional Anthropomorphic Skull Phantom" Biosence® Nov. 1999).

MED–TEC, Inc., VAC–LOK™ Patient Immobilization System (1996).

Lattanzi, J.P., et al., "A Comparison of Daily C T Localization to a Daily Ultrasound Based System (BAT™) in Prostate Carcinoma—Will BAT Fly?", *I.J. Radiation Oncology Bio.Phys.*, vol. 42, No. 1, p 215 (Suppl. 1998).

Lax, I., et al., "Stereotactic Radiotherapy of Malignancies in the Abdomen," *Acta Oncologica*, vol. 33, No. 6, pp 677–683 (1994).

Lax, I, et al., "Stereotactic Radiotherapy of Extracranial Targets," *Z. Med. Phys.*, vol. 4, pp 112–113 (1994).

Lax, I., et al., "Extracranial Stereotactic Radiosurgery of Localized Targets," *Journal of Radiosurgery*, vol. 1, No. 2, pp 135–148 (1998).

Lederman, G., et al., Editors: "Body Radiosurgery Results," *J. of Radiosurgery*, www.siuh.edu.radoncology/results, 1998a.

Lederman, G., et al., Editors: "Fractionated Stereotactic Body Radiosurgery at Staten Island University Hospital,". *of Radiosurgery*, www.siuh.edu.radoncology/bodyrs, 1998c.

Lederman, G., et al., Editors: "Innovative Treatment for Pancreas Cancers," *J. of Radiosurgery*, www.siuh.edu.radoncology/pancancer, 1998d.

Lederman, G., et al., Editors: "Fractionated Stereotactic Body Radiosurgery, an Innovative and Effective New Treatment Method," *J. of Radiosurgery*, www.siuh.edu.radoncology/bodyrad, 1998e.

Lederman, G., et al., Editors: "Stereotactic Radiosurgery (BSR) for Extracranial Metastases," *J. of Radiosurgery*, www.siuh.edu.radoncology/estracran, 1998g.

Lederman, G., et al., Editors: "Body Stereotactic Radiosurgery (BSR) for Primary Extracranial Tumors," *J. of Radiosurgery*, www.siuh.edu.radoncology/extracrantumor, 1998.

Lederman, G., et al., Editors: "Body Radiosurgery Treatment Procedure," *J. of Radiosurgery*, www.siuh.edu.radoncology/bradprocedure, 1998.

Naslund, I., et al., "New Prostate Repositioning Paradigm—a Whole Body Frame for Conformal Radiotherapy Techniques, with Vertical Patient Alignment and Rotation to a Horizontal Position," *I.J. Radiation Oncology/Biology/Physics*, vol. 39, No. 2, Suppl Abstract No. 2176 (1997).

Onik, G., et al., "CT Body Stereotaxic Systems for Placement of Needles Arrays," *Int. J. Radiation Oncology Biol. Phys.*, vol. 14, pp 121–128 (1987).

Sato, M., et al., "Feasibility of Fameless Stereotactic High–Dose Radiation Therapy for Primary or Metastatic Liver Cancer," *J of Radiosurgery*, vol. 1, No. 3, pp 233–238 (1998).

Stea, B., et al., "Spinal Stereotactic Radiosurgery: a Phase–1 Study," *I. J. Radiation Oncology Bio. Phys.*, vol. 42, No. 1, p 214 (Supplement 1998), Abstract No. 1011.

Wulf, J., et al., "Hypofractionated, High–Dose Radiation Under Stereotactic Conditions in the Stereotactic Body Frame: Accuracy of Repositioning at 11 CT–Simulations and 37 Applications at the LINAC," *I.J. Radiation Oncology Bio. Phys.*, vol. 42, No. 1, p 215 (Supplement 1998) Abstract No. 1013.

BIONIX Co., "Reusable/Disposable Frame Head Immobilizer," Advertisement (Apr. 1996).

BIONIX Co., "Pelvis/Belly Board Immobilizer," Advertisement (Apr. 1996).

BIONIX Co., "3–D Pelvis Board Immobilizer," Advertisement (Apr. 1996).

MED–TEC, Inc. "HipFix® Hip & Pelvic Immobilization System" Advertisement (1996).

MED–TEC, Inc. "REDI–FOAM Foam Immobilization System" Advertisement (1996).

Precision Therapy International Stereotactic Body Frame™ Dose escalation by Precision Conformal Radiotherapy, Advertisement (Sep. 1995).

Pfizer—Leibinger® Extracranial Radiosurgery, Advertisement (1997).

Ferrero, R., "Consider Using Resolvers and Synchros," *Electronic Design*, vol. 17, pp70–72 (1975).

Goldberg, A., et al., "Hypofractionated Body Radiosurgery (HBR) as Treatment of Primary Pancreas Cancers," *J. RadiosurgeryI*, vol. 1, No. 1, pp 63–74 (1998) Abstract siuh.edu.radoncology/hypocancer.

Hamilton, Allan J., "Preliminary Clinical Experience with Linear Accelerator–Based Spinal Stereotactic Radiosurgery," *Neurosurgery*, vol. 36, No. 2, pp 311–319 (1995).

Lutz, W., et al., "A System for Stereotactic Radiosurgery with a Linear Accelerator," *Int. J. Radiation Oncology Biol. Phys.*, vol. 14, pp 373–381 (Feb. 1988).

Hamilton, A.J., "LINAC–Based Spinal Stereotactic Radiosurgery," *Amer Soc. for Stereotactic and Functional Neurosurgery*, p. 69 (Mar. 10, 1995) Abstract.

Hamilton, A.J., et al., "Phase 1 Prototype Device for Sinal Stereotactic Radiosurgery," *LINAC Radiosurgery—1995*, p 83, paper No. 49, Dec. 6–10, 1995.

Hamilton, A.J., et al., "Spinal Stereotactic Radiosurgery: A Viable Treatment Strategy for Spinal Neoplasms Failing Standard Fractionated Radiotherapy?" *Int'l Stereotactic Radiosurgery Society*, 3rd Congress, p. 55, paper No. 29 Abstract (Jun. 27, 1997).

Hamilton, A.J., Chapter 92: Linear Accelerator (LINAC)–Based Stereotactic Spinal Radiosurgery, *Textbook of Stereotactic and Functional Neurosurgery*, McGraw–Hill pp 857–869 (1998).

Hanselman, D.C., "Resolver Signal Requirements for High Accuracy Resolver–to–Digital Conversion," *IEEE Transactions on Industrial Electronics*, vol. 37, No. 6, pp 556–561 (Dec. 1990).

Herfarth, K.K., et al., "Extracranial Stereotactic Conformal Radiation Treatment of Tumors in the Liver and the Lung," *I. J. Radiation Oncology Bio Phys.*, vol. 42, No. 1, p 214 (Suppl. 1998).

* cited by examiner

WHOLE BODY STEREOTACTIC LOCALIZATION AND IMMOBILIZATION SYSTEM

CROSS-REFERENCE TO RELATED APPLICATIONS

This application is a continuation-in-part application of U.S. patent application Ser. No. 09/477,397, entitled "Whole Body Stereotactic Localization System," filed on Jan. 4, 2000, now abandoned, which application claimed the benefit of the filing of U.S. Provisional Patent Application Ser. No. 60/114,942, entitled "A Whole Body Stereotactic Localization System With Imaging Resolver Apparatus and Method for Stereotactic Alignment," filed on Jan. 4, 1999, and the specifications thereof are incorporated herein by reference.

BACKGROUND OF THE INVENTION

1. Field of the Invention (Technical Field)

The present invention relates to medical equipment and methods, more particularly to equipment and methods for radiation therapy including stereotactic localization and immobilization systems and methods.

2. Background Art

Fractionated radiation therapy to a target lesion within the body is the primary method used for radiation therapy. This method requires precise immobilization and repositioning of the patient for other treatment sessions. Stereotactic localization and procedures on cranial and extra-cranial body parts have a similar requirement.

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

The need for effective patient immobilization techniques for radiation therapy has recently inspired the development and use of many immobilization devices in that field. The ability to reposition the patient and the patient's ability to maintain the position during treatment may be improved with the use of immobilization devices (see Bentel 1999). Immobilization reduces "normal tissue" complication rate, allows increased irradiation, and improves tumor control rate. "A modest increase of the treatment and isodose margin can have a significant effect on the volume of normal tissue exposed" (see Bentel 1999). Historically, skin marks, or marker systems (see U.S. Pat. No. 4,583,538, to Onik, et al.), have been used to aid in target localization and repositioning. Skin marks used for patient repositioning may migrate as they are re-marked and markings can shift with respect to underlying deeper tissues. They also tend to smear and fade. Markings on a body immobilization device do not move with respect to the target, they do not smear or fade, hence the problems of re-marking and migration are eliminated (see Bentel 1999). Markings on the immobilization device may also be matched to skin markings (see Bentel 1999).

Patient comfort, ability to easily maintain the position for extended periods of time, reproducibility of the patient's "prescription" position, and anticipated beam orientation are essential in successful repeat radiotherapy treatments (see Bentel 1999). Comfort allows the patient to relax in a position throughout the treatment period, discouraging body movement caused by fatigue or discomfort. Patient movement could invalidate target localization and expose healthy tissue to unwanted radiation. Some patients, especially children, may move as much as 5 mm (or more) during treatment (due to pain or an uncomfortable position or because they are uncooperative, demented or restless) (see Bentel 1999). Goitein and Busse studied the theoretical effect of under dosage at the perimeter of the treatment field caused by random immobilization errors. They found that as much as a 12% improvement of tumor control probability could be achieved by good Immobilization techniques (see Bentel 1999). In addition, a cost reduction is realized over traditional radiation therapy because the number of port films as well as setup time is reduced which allows for more patient throughput (see Bentel 1999).

Because body fixation is essential for controlled radiation therapy during cancer treatment (Lederman, et al. 1998), emphasis has been placed on non-invasive and comfortable means of body immobilization and repositioning (see Bentel 1999). New techniques for precision radiation to extracranial targets of the body have been developed for highly successful treatment of lesions. External fixation systems are used to localize the body for exact repositioning during repeat treatments. The concept of stereotactic localization has been used to localize and aid in the target positioning for radiotherapy (see Lax, et al. 1994 and Hamilton, et al 1995).

Bentel (Bentel 1999) references a concept of three-dimensional localization (stereotactic localization) when she states that "The coordinate system allows one to describe the location of any point with respect to another known point (origin). Three axes (x,y,z) transect this known point. The location of any point with respect to the origin is described by the distance measured along each axis and by indicating on which side of the axis the point is located." These concepts are fundamental to the principles of stereotactc localization, which is to determine the location of deep body structures which are invisible from the surface but their location can be determined by a knowledge of their three-dimensional coordinates in space relative to known anatomical and topographical landmarks in a volumetric space defined by a stereotactic instrument. The stereotactic technique seeks to avoid disturbance to surrounding structures during therapeutic interventions by the use of minimally invasive precision localization Instruments. Guiot, G. and Derome, P., "The principles of stereotactic thalamotomy", *Correlative Neurosurgery*, edited by Kahn, E J et al., Springfield, Ill., $2^{nd}$ Edition, Chapter 18, pp. 376–401, 1969.

As noted by Bentel and Marks (Bentel, et al. 1997) and Bentel (Bentel 1999), a number of methods have been historically used for patient immobilization during radiation therapy. More recently the concept of stereotactic localization, which has previously been successfully applied to radiotherapy/radiosurgery of the brain (see Lutz, et al. 1988), has been applied to extracranial radiotherapy target areas. (Lax 1994, Lederman 1998, and Hamilton, et al., 1995 and 1997).

This method of patient immobilization and stereotactic localization has been found to be more effective than previous localization methods for radiation therapy. Lax, et al. (Lax, et al. 1994), found a high degree of target reproducibility when using a stereotactic body frame. They found, from repeat CT examinations of patients in the body frame, a 5 mm range (i.e., a 2–7 mm range of error) of target volume positioning for targets in the liver and lungs. In addition, local tumor control of 90% was possible using this technique (see Blomgren, et al. 1995). The clinical use of a stereotactic body frame is increasing because it can be used to treat lesions over a wide variety of body areas (see Lederman, et al. 1998a–g).

Additional references providing important background to the present invention include the following U.S. Pat. No. 3,783,251, to Pavkovich, et al.; U.S. Pat. No. 4,583,538, to Onik, et al.; U.S. Pat. No. 4,638,798, to Shelden, et al.; U.S. Pat. No. 4,341,220, to Perry; U.S. Pat. No. 4,608,977, to Brown, et al.; U.S. Pat. No. 4,618,978, to Cosman, et al.; U.S. Pat. No. 5,099,846, to Hardy, U.S. Pat. No. 5,553,112, to Hardy, et al.; U.S. Pat. No. 5,143,076, to Hardy, et al.; U.S. Pat. No. 5,176,689, to Hardy, et al.; U.S. Pat. No. 5,398,684, to Hardy, et al.; U.S. Pat. No. 5,354,314, to Hardy, et al.; and U.S. Pat. No. 6,011,828, to Hardy, et al. Other background publication include: Bentel, G. C., "Central Nervous System," *Patient Positioning and Immobilization in Radiation Oncology*, New York: McGraw-Hill, 1999, pp. 71–92; Bentel, G. C., "General Consideration of Positioning and Immobilization," *Patient Positioning and Immobilization in Radiation Oncology*, New York: McGraw-Hill, 1999, pp. 23–38; Bentel, G. C., "Treatment Accuracy and Precision," *Patient Positioning and Immobilization in Radiation Oncology*, New York: McGraw-Hill, 1999, pp. 11–22; Bentel, G. C., "Treatment Geometry," *Patient Positioning and Immobilization in Radiation Oncology*, New York: McGraw-Hill, 1999, pp. 1–10; Bertolina, J. A., et al., "Quality Assurance Testing for An Extracranial Stereotactic Device: Methods and Results," Poster No. 129, Intl Stereotactic Radiosurgery Society, 1997, p. 233; Blomgren, H., et al., "Radiosurgery for Tumors in the Body: Clinical Experience Using a New Method," *J. of Radiosurgery*, Vol. 1:1, pp. 63–74, 1998; Ferrero, R., "Consider using resolver and synchros," *Electronic Design*, Vol. 17, 1975; Goldberg, A., et al., "Hypofractionated Body Radiosurgery (HBR) As Treatment Of Primary Pancreas Cancers," *J. of Radiosurgery*, www.siuh.edu.radoncology/Hypocancer, 1998; Hanselman, D., "Resolver Signal Requirements for High Accuracy Resolver-to-Digital Conversion," *IEEE Transactions on Industrial Electronics*, Vol. 37, No. 6, pp. 556–561, 1990, Hamilton, A. J. , "LINAC-Based Spinal Stereotactic Radiosurgery," 1995 Quadrennial Meeting of the American Society for Stereotactic and Functional Neurosurgery, 1995, p. 69; Hamilton, A. J., et al., Paper No. 49—"Phase I Prototype Device for Spinal Stereotactic Radiosurgery," Intl Stereotactic Radiosurgery Society, 3rd Congress, 1997a, p. 83; Hamilton, A. J., et al., Paper No. 29—"Spinal Stereotactic Radiosurgery: A Viable Treatment Strategy for Spinal Neoplasms Failing Standard Fractionated Radiotherapy," Intl Stereotactic Radiosurgery Society, 1997b, p. 55; Hamilton, A. J., "Linear Accelerator (LINAC)-Based Stereotactic Spinal Radiosurgery," in Gildenberg, P. L. et al., eds, *Textbook of Stereotactic and Functional Neurosurgery*, New York: McGraw-Hill, 1998, pp. 857–869; Herfath, K. K., et al., "Extracranial Stereotactic Conformal Radiation (3 Treatment of Tumors in the Liver and the Lung," *I.J. Radiation Oncology Bio Phys*, Vol. 42:1, p. 214, Supplement 1998; Lattanzi, J. P., et al., "A Comparison of Daily CT Localization To A Daily Ultrasound Based System (BAT™) In Prostate Carcinoma. Will BAT Fly?", *I.J. Radiation Oncology Bio Phys*, Vol. 42:1, p. 215, Supplement 1998; Lax I., et al., "Stereotactic Radiotherapy Of Malignancies In The Abdomen—Methodological aspects," *Acta Oncologica*, 33:677–683, 1994; Lax, I., et al., "Stereotactic Radiotherapy Of Extracranial Targets," *Med. Phys*, pp. 112–113, 1994; Lax, I., et al., "Extracranial Stereotactic Radiosurgery of Localized Targets," *J. Of Radiosurgery*, Vol.1:2, pp. 135148, 1998; Lederman, G. et al., eds: "Body Radiosurgery Results", *J. of Radiosurgery*, www.siuh.edu.radoncology/bradresults, 1998a; Lederman, G. et al., eds: "Body Radiosurgery Treatment Procedure," *J. of Radiosurgery*, www.siuh.edu.radoncology/bradprocedure, 1998b; Lederman, G. et al., eds: "Fractionated Stereotactic Body Radiosurgery at Staten Island University Hospital," *J. of Radiosurgery*, www.siuh.edu.radoncology/bodyrs, 1998c; Lederman, G. et al., eds: "Innovative Treatment For Pancreas Cancers," *J. of Radiosurgery*, www.siuh.edu.radoncology/pancancer, 1998d; Lederman, G. et al., eds: "Fractionated Stereotactic Body Radiosurgery, An Innovative & Effective New Treatment Method," *J. of Radiosurgery*, www.siuh.edu/radoncology/bodyrad, 1998e; Lederman, G., et al., "Body Stereotactic Radiosurgery (BSR) For Extracranial Metastases," *J. of Radiosurgery*, www.siuh.edu.radoncology/Extracran, 1998f; Lederman, G., et al., "Body Stereotactic Radiosurgery (BSR) For Primary Extracranial Tumors," *J. of Radiosurgery*, www.siuh.edu.radoncology/extracrantumor, 1998g; Sato, M., et al., "Feasibility of Frameless Stereotactic High-Dose Radiation Therapy for Primary or Metastatic Liver Cancer," *J. of Radiosurgery*, Vol. 1:3, pp. 233–238, 1998; Stea, B., et al., "Spinal Stereotactic Radiosurgery: A :Phase-I Study," *I.J. Radiation Oncology Bio Phys*, Vol. 42:1, p. 214, Supplement 1998; Onik, G., et al., "CT Body Stereotactic System for Placement of Needle Arrays," *Int. J. Radiation Oncology Biol. Phys.*, Vol. 13, pp. 121–128, 1987; Wulf, J., et al., "Hypofractionated, High-dose Radiation Under Stereotactic Conditions in the Stereotactic Body Frame: Accuracy of Re-positioning At 11 CT-Simulations And 37 Applications At The LINAC," *I.J. Radiation Oncology Bio Phys*, Vol. 42:1 p. 215, Supplement 1998; Lutz, W., et al., "A System of Stereotactic Radiosurgery with a Linear Accelerator," *Int'l J. Radiation Oncology & Biological Physics*, Vol. 14, pp. 37381 (1988); Hardy, T. L., et al., "CASS: *A Program for Computer Assisted Stereotaxic Surgery*," Proceedings of the Fifth Annual Symposium on Computer Applications in Medical Care, Nov. 1981; Galloway, R. L., Jr., "*Orientation and Registration of Three-Dimensional Images*," Textbook of Stereotactic and Functional Neurosurgery (1997); Galloway, R. L., Jr., "*Frameless Stereotactic Systems*," Textbook of Stereotactic and Functional Neurosurgery (1997); Parkinson, A. R., et al., "OPTDES.BYU: *A Software System for Optimal Engineering Design*," Proceedings of ASME International Computers in Engineering Conf., Las Vegas, Nev., August 1984); Parkinson, A. R., et al., "*Consideration of Worst-Case Manufacturing Tolerances in Design Optimization*," Transactions of the ASME, Vol. 108, December 1986. Advertising Literature providing additional background includes: Reusable/Disposable Frame Head Immobilizer, BIONIX Co. (April 1996); Pelvis/Belly Board Immobilizer, BIONIX Co. (April 1996); 3-D Pelvis Board Immobilizer, BIONIX Co. (April 1996); HipFix Hip & Pelvic Immobilization System, MED-TEC Inc. (1995); Vac-Lok Patient Immobilization System, MED-TEC, Inc. (1996); Redi-Foam Foam Immobilization System, MED-TEC, Inc. (1996); Stereotactic Body Frame Dose escalation by precision conformal radiotherapy, Precision Therapy International (September 1995); Extracranial Radiosurgery, Leibinger (1997); Uni-Frame Head Immobilization System, MED-TEC, Inc. (1996); Alpha Cradle brand Patient Repositioning Systems, Smithers Medical Products, Inc. (1995); IZI Medical Products Corp. World Wide Web Home Page (September 1999); Biosense Magellan Image-Guidance for Brain, Spine, and Sinus Surgery (date unknown); and Computerized Imaging Reference Systems, Inc., 3D Skull Phantom (November 1999).

The present invention is of a system for use in the field of medicine and primarily for fractionated stereotactic radiotherapy/radiosurgery and other stereotactic procedures. The system is an external whole body immobilization and stereotactic localizer system. The term 'whole body' refers to all or some portion of the body of the patient. The term 'stereotactic localization system' as used in the art of stereotactic treatment particularly of the patient's brain, generally includes some means for immobilizing the patient's cranium and is thus part of the 'stereotactic localization system'; however, in this application the term 'whole body immobilization' system is used as a complement to the 'stereotactic localization system;' the two systems comprise the present invention. It gives a high degree of precision target localization for whole body stereotactic procedures including biopsy and radiotherapy with a unique imaging resolver fiducial localization method. As noted above, the need for effective patient immobilization has become widely recognized in recent years, particularly as the application of conformal radiation treatment techniques (where small treatment margins are possible) has increased. (Bentel, 1999 pp. 23–38). Stereotactic conformal radiotherapy with dose escalation to the targeted lesion is improved with this accurate and reproducible target localization system. Head, neck, thoracic, abdominal, or pelvic localization is possible with the present invention, which may be extended to include the entire body.

The present invention is of a body immobilization and stereotactic localization frame and method comprising use of a non-invasive device for immobilizing a human body from head to pelvis comprising form fitting custom molds for both anterior and posterior portions of the body. In the preferred embodiment, the posterior mold is a vacuum mold or polyurethane foam mold and the anterior mold is a thermoplastic mold, both being reusable over the course of a fractionation or other treatment regimen for the subject patient. The frame comprises two or more imaging localization fiducials each having a repetitive trigonometric waveform wherein one of the two fiducials is offset along the longitudinal axis of the frame relative to the position of a second of the fiducials. The two or more imaging localization fiducials additionally include quality assurance fiducials placed in opposing pairs at predetermined laterally spaced positions parallel to the longitudinal axis of the frame. The word "fiducial" means "designating a line, point, etc. assumed as a fixed basis of comparison". 1 New Shorter Oxford English Dictionary, 942 (Clarendon Press, Oxford England) (1993 Ed.). A fiducial is made from a material (as defined below) that appears in an image as a marker to indicate its location used in the determination of the image stereotactic coordinates.

The present invention is also of a stereotactic localization frame and method employing an imaging resolver (as subsequently defined) comprising a continuous array of coupled fiducials. In the preferred embodiment, two or more imaging localization fiducials have a repetitive waveform, preferably a trigonometric wave form such as a sine or cosine waveform, and most preferably the two fiducials are longitudinally offset by a $\pi/2$ distance. A non-invasive device for immobilizing a human body from head to pelvis is employed comprising form fitting custom molds for both anterior and posterior portions of the body.

The present invention is further a radiation treatment regimen comprising: using a stereotactic body frame with imaging resolver; forming posterior and anterior body molds of a patient for use in the frame; aligning the frame in an imaging gantry; taking images of the patient; transporting the images to computer treatment planning system; calibrating the images; performing volumetric determinations; determining stereotactic position of one or more volumes within the body; composing a radiation treatment plan to effectively treat one or more volumes within the body; aligning the patient, body molds, and frame in a radiation treatment facility; and treating the patient according to the plan. In the preferred embodiment the aligning and treating steps may be repeated for the same patient one or more additional times and other stereotactic treatment plans may be performed.

The system of the invention was developed to meet the fundamental requirements of body immobilization and stereotactic localization in a non-invasive manner. In addition, the invention is capable of immobilizing the head and neck as well as the thoracic, abdomen, and pelvis. Its fiducial localizer system is continuous from head to pelvis and allows accurate and continuous stereotactic imaging and localization throughout the entire upper body and by simple extensions it can be used for localization of the entire body. The advantages of the invention are increased accuracy, reliability, and whole body localization. Immobilization is achieved by the use of a vacuum mold system or polyurethane foam mold for posterior (the part of the body nearest the frame base) areas and a thermoplastic body mold to cover large body surfaces in the ventral or anterior plane. The method of combined anterior and posterior form fitting custom molded immobilization, which cover wide surface areas of the body, improves immobilization and repositioning as well as minimizing diaphragmatic and abdominal movements. The vacuum or foam molds and the thermoplastic molds can be stored and reused for each patient in a radiation fractionation or other treatment regimen. All components of the invention, including the visible frame coordinates and scales, provide for precise target treatment.

The localization features of most stereotactic frames are similar, differing mainly in the organization of the coordinate system of the frame and its mechanical dimensions. All stereotactic frames are created for the purpose of immobilization, precise patient repositioning, and localization of volume structures or lesions within the volumetric space defined by the frame and the immobilized body part. With regards to stereotactic frames, the general convention is that the long axis of the body (longitudinal axis) is given the designation of the z-axis in the Cartesian coordinate system of three-dimensional spatial localization. The left-right transverse axis is generally designated as the x-axis and the anterior/posterior (vertical) axis is designated as the y-axis. Most conventional stereotactic frames use incremental indicators in millimeters and centimeters along each axis for precise coordinate referencing. The aim of the stereotactic frame system of the present invention is to permit a wide area of body immobilization and allow precise stereotactic imaging and positioning of body areas within the frame.

The word "waveform" is used to refer to a "wave regarded as characterized by a particular shape or manner of variation. esp. a varying voltage," 2. The New Shorter Oxford English Dictionary, 3638 (Clarendon Press, Oxford, England) (1993 Ed.), and refers to one period or phase length. A "repetitive waveform", refers to a repeating series of the waveform.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The present invention is a whole body stereotactic localization system with an imaging resolver apparatus and method for stereotactic alignment. More particularly, the present invention relates to a method and apparatus for precisely imaging structures or volumes (target volumes) within a patient's body and realigning the position of target volumes for the purpose of stereotactic treatment planning. Such treatment planning can include biopsies, radioisotope implantation, surgical procedures, radiosurgery/stereotactic radiation therapy, or such other diagnostic or therapeutic measures that may be required by a medical practitioner.

The invention permits aligning and imaging a body part by immobilizing the body part within a stereotactic body localization system having an imaging resolver fiducial localizer for precise imaging and localization of the body parts within the apparatus. The system comprises a frame including a base and sides with an imaging localization fiducial arrangement (imaging resolver) embedded in its base and sides. The base frame is preferably manufactured from polycarbonate, or other durable and versatile thermoplastic or similar material having a low radiation beam attenuation.

The invention also comprises a software program for calculation of stereotactic coordinates from scanner images taken with the invention. The preferred computer system for use with the invention is an IBM or IBM-compatible PC computer running under Microsoft® Windows, although any personal computer, workstation, or mainframe operating under any reliable operating system is acceptable.

Figure 3:
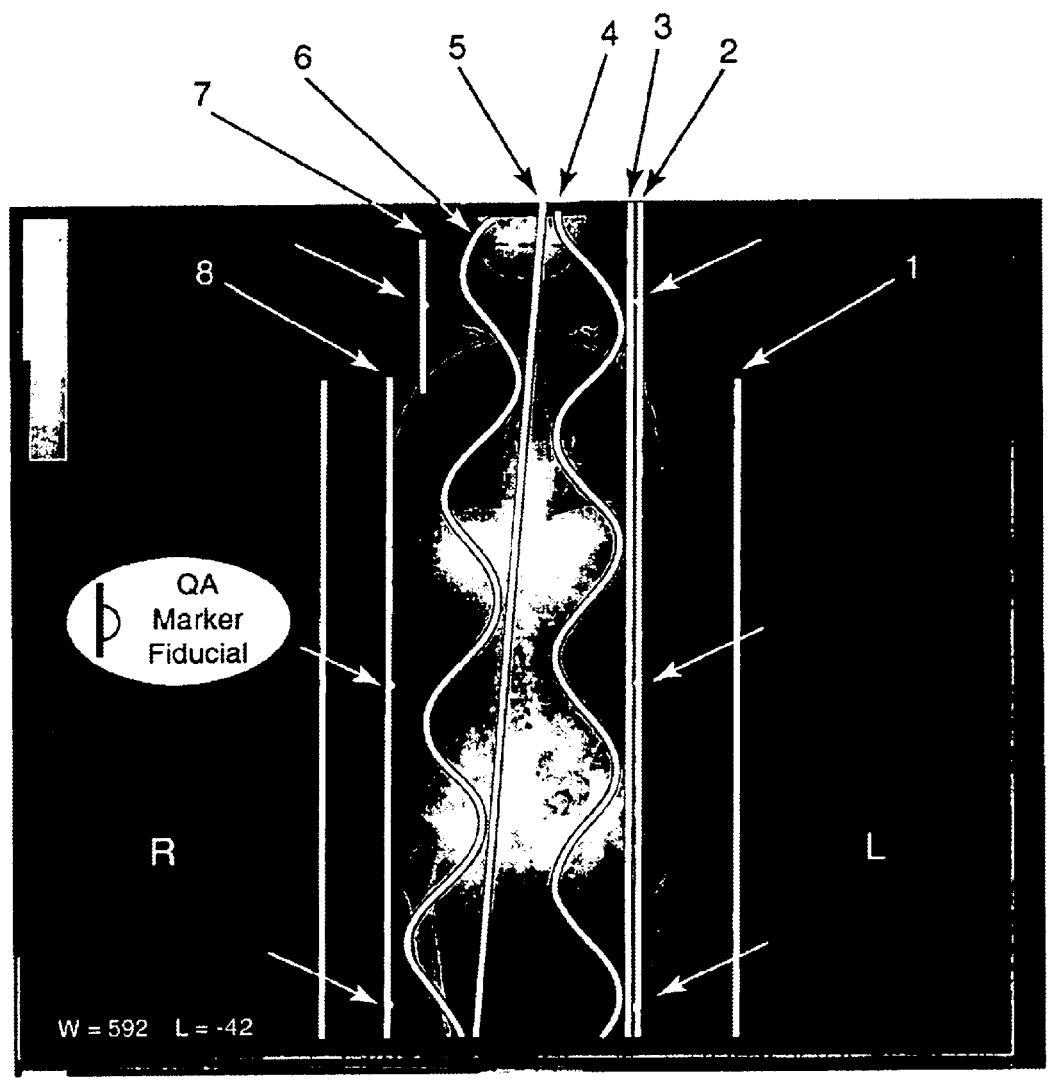
FIG. 3 is a CT scout film of a patent placed in the frame of the invention showing the fiducial localization system in the base; quality assurance (QA) markers (white arrows) are at z=100, 500, and 900; the two vertical closely parallel fiducials identify the left side of the frame of the invention.
Figure 4:
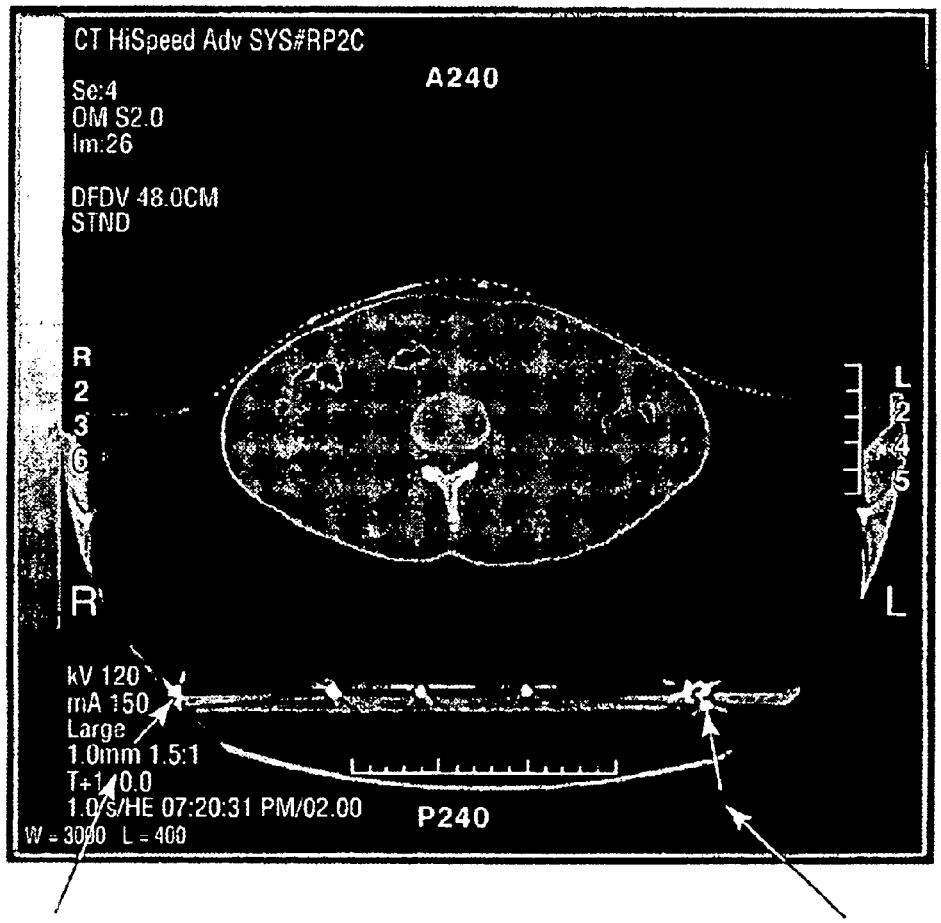
FIG. 4 is a QA image taken at z=500; note QA markers in the base of the frame (white arrows)

Referring to FIGS. 6–9 and 2(a)–2(d), preferred mechanical components of the invention include the base frame and fiducial system 11 with hand-holder recesses 14, an overarm 18 (arc) that can be positioned at various positions along the z-axis, and built-in quality assurance markers (see FIGS. 3–4) which are placed in opposing pairs at specific positions along the z-axis of the system. Supplementary components of the invention include a polyurethane foam mold or vacuum immobilization system 13 placed along the base of the frame of the invention, a thermoplastic mold 17 with handles (FIG. 2(d)), and a headrest 15. The system also preferably comprises a scale along the x-axis 21, a combined x and y-axis scale 22, a z-axis scale 23, a y-axis scale 24, and a window 26 in the arcto view and set the position of the arc along the z-axis.

The present invention improves upon the less versatile localizers manufactured by Elekta Instrument AB and Howmedica (Leibinger). The Elekta Stereotactic Body Framers is limited to treatment of targets in the abdominal, thoracic and pelvic regions and uses a saltatorial, non-continuous fiducial arrangement having limited accuracy with a high incidence of undetectable errors. The Elekta system is non-invasive but does not handle procedures on the head and neck. Immobilization is achieved by the limited use of a vacuum mold for posterior immobilization only (that portion of the body nearest the frame's base). (Precision Therapy brochure 1995, Lax, et al., 1994a and b and 1998, and N äslund, et al., 1997). An uncomfortable breastplate must be used with pressure against the sternum for reduction of diaphragmatic movements. The Howmedica (Leibinger) system uses a substantially equivalent method of immobilization, but requires an invasive method for spinal fixation (Hamilton, et al., 1995 and 1997).

Figure 1:
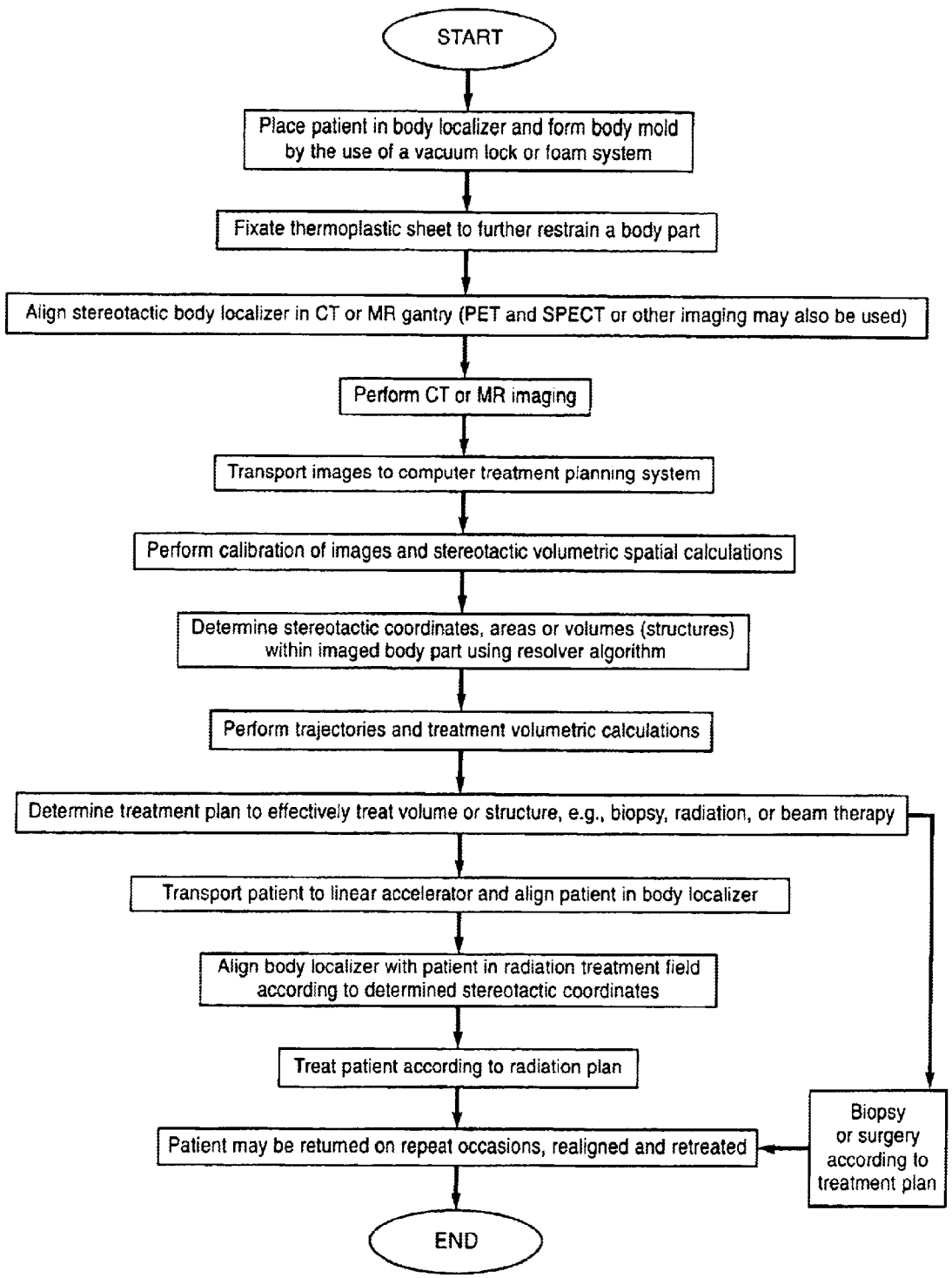
FIG. 1 is a flow diagram of the preferred method of the invention.
Figure 2B:
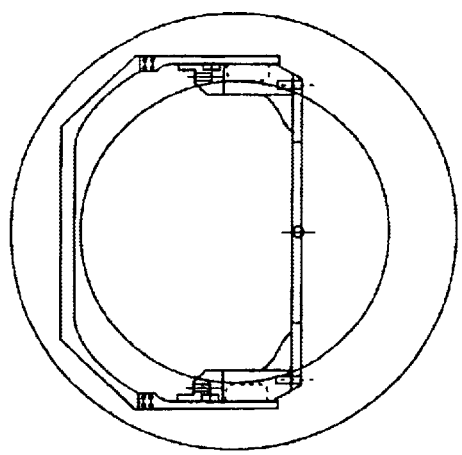
FIGS. 2(a)–2(d) are side, end, top, and thermoplastic sheet holder views of the preferred frame of the invention.
Figure 2D:
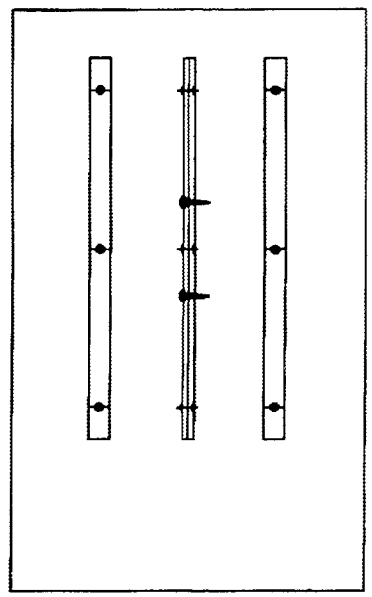
Figure 2A:
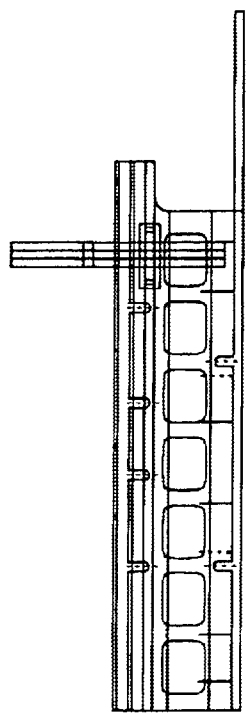
Figure 2C:
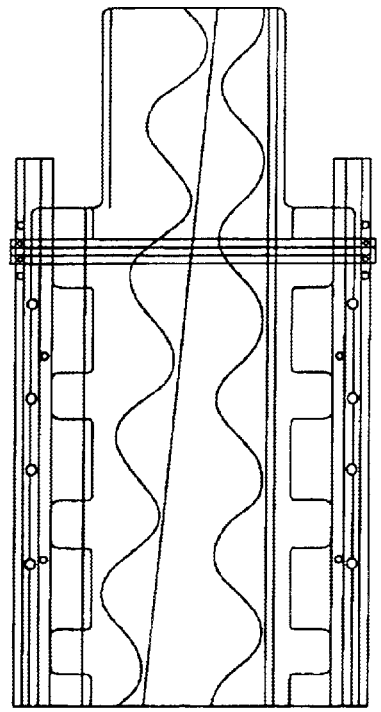

Referring to FIG. 1, the preferred method of the invention comprises the following steps:

a. Place patient in body localizer and form body mold by use of a vacuum lock or foam system;

b. Affix thermoplastic sheet;

c. Align stereotactic body localizer in CT, MR gantry, using imaging system laser alignment lights (Angiographic, PET or SPECT imaging can be used);

d. Perform CT or MR images (Angiographic, PET or SPECT imaging can be used);

e. Transport images to computer treatment planning system;

f. Perform calibration of images;

g. Perform volumetric determinations;

h. Determine stereotactic position of volumes within imaged body part, using resolver algorithm;

i. Determine biopsy or radiation treatment plan to effectively treat volume of structure or lesion;

j. Transport patient to linear accelerator for radiation therapy;

k. Align body localizer with patient and radiation treatment field, according to stereotactic points previously defined; and l. Treat patient according to biopsy or radiation treatment plan. Patient may be returned on repeat occasions, realigned and retreated.

Non-invasive or minimally invasive surgery has become more widely accepted and therefore more popular in recent years. Stereotaxy plays an essential role in this type of surgery. The use of a rigid fixation device to acquire images and provide positioning of the patient is fundamental to stereotaxy. Because of the size of the head in comparison to the size of the body, a localization system that surrounds the head and provides the coordinate localization that one needs for positioning is quite different than for the body. Although sub-millimeter accuracy is not needed for the body as it is for the head, the localization system should provide accuracy within 5 mm or less and should have a high degree of error detection.

The imaging resolver fiducial array in the preferred embodiment is arranged on the plane (base) of the stereotactic frame. This arrangement requires orthogonal alignment of the stereotactic body frame in the imaging scanner gantry. Alternatively, the imaging resolver may be placed in multiple planes about the body so as to avoid this requirement. In the preferred embodiment, the X (right-left) and Y (anterior-posterior) coordinates can be calculated by determining the size of a millimeter in each of these directions. This can be done using the fixed fiducials of a preset size that are present along the sides and the back of the body. The Z (superior-inferior) coordinate can be calculated using the angled (or angled and sine-cosine) fiducials on the back (or bottom) of the localizer.

The use of the present invention requires that the user is provided with a method of calibrating the CT and/or MR images (Angiographic, PET and SPECT imaging can also be used) taken through the body frame for localization purposes. This requirement is best fulfilled with user-friendly computer software, but may also be determined from direct readings of fiducial locations determined from the scanner console.

Figure 10:
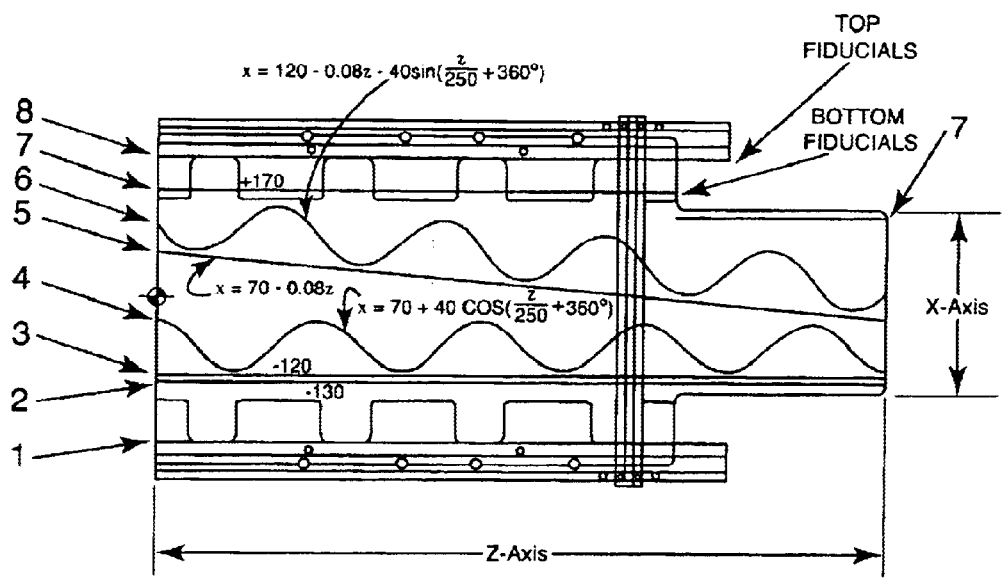
FIG. 10 illustrates the fiducial geometry of the invention with arrows pointing to fiducials numbered 1 to 8.

FIG. 10 illustrates the preferred fiducial geometry of the invention with preferred fiducials 1,2,3,4,5,6,7,8. The central three fiducials 4,5,6 constitute the imaging localization resolver along the z-axis. The arrangement comprises:

a) an origin as marked by the circle with the quadrants;

b) a centrally placed diagonal fiducial 5 the position and slope of which is mathematically defined as x=70−0.08z, located between;

c) a cosine wave fiducial 4 which is defined as x=−70+40cos((z/250)*360°); and d) a sine wave fiducial 6 which is defined as x=120−0.08z40sin((z/250)*360°).

The position and specific waveforms of the fiducials 4, 5 and 6 should be understood to be merely exemplary of the preferred fiducial geometry of the invention.

Thus, any orthogonal plane intersecting the z-axis, which is parallel to the x-axis, has the z positional value determined as discussed below.

The resolver has at least two fiducials, 4, 6, that are oriented generally parallel to the z-axis of the frame and laterally spaced apart. Each fiducial has a repetitive trigonometric waveform. In the preferred embodiment the first waveform 4, is a cosine function and the second waveform 6 is a sine function. The position of the second fiducial waveform, 6, is longitudinally offset to the position of the first fiducial waveform, 4. The offset, expressed angularly, is $\pi/2$. Therefore, an axial image plane (x, y) will intercept both fiducial waveforms at complementary locations assuring a phase angle of 45 degrees at one of the intersections. The straight line or third fiducial 5 is positioned non-parallel to the z-axis and is laterally positioned between fiducials 4, 6. Fiducials 7, 8, are quality assurance fiducials and are straight lines parallel to the longitudinal z-axis of the frame and are used as an error check to differentiate the patient's left hand side from the right hand side where fiducials 2, 3 are positioned.

Figure 5:
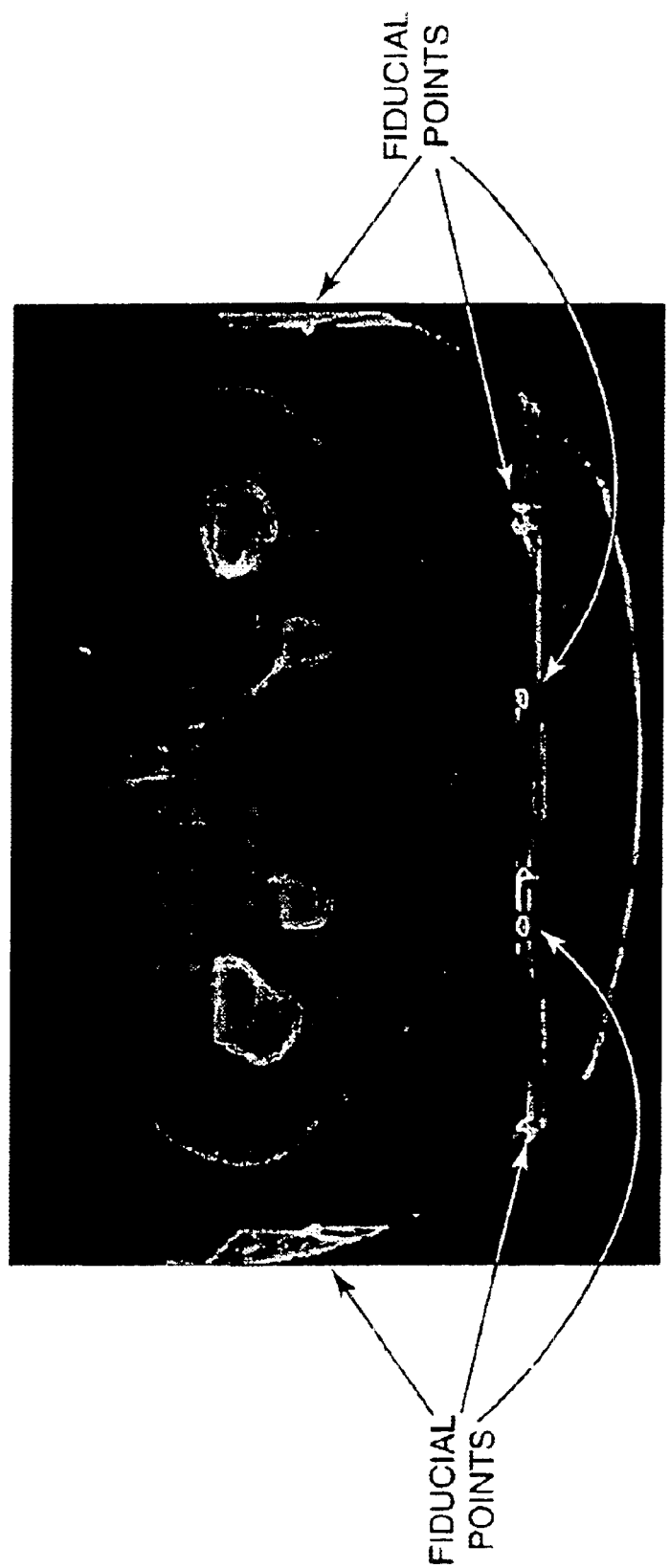
FIG. 5 is an axial image taken at z=275 in the low pelvic region; note fiducials in the base and sides of the frame.
Figure 6:
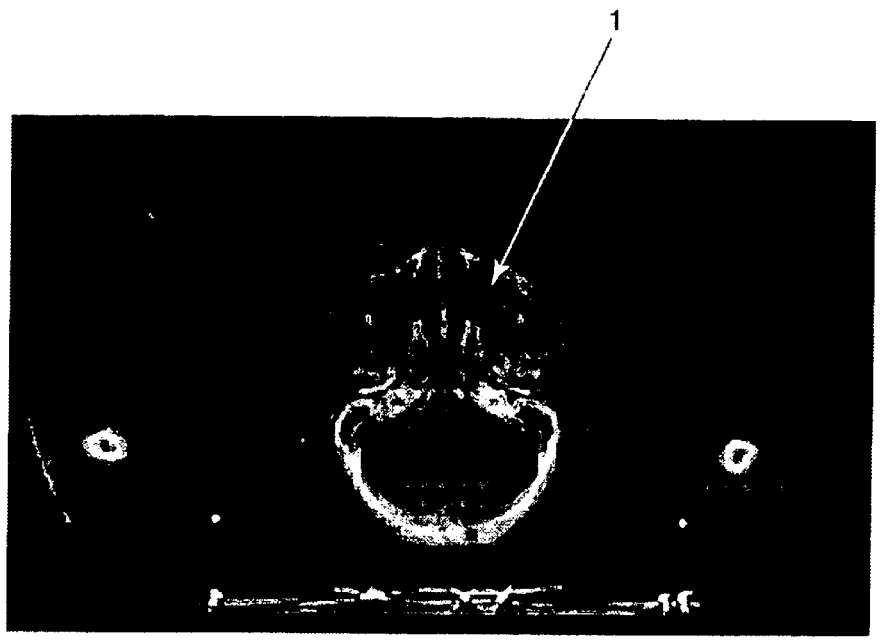
FIG. 6 is an axial image taken at z=998 in the head region.
Figure 7:
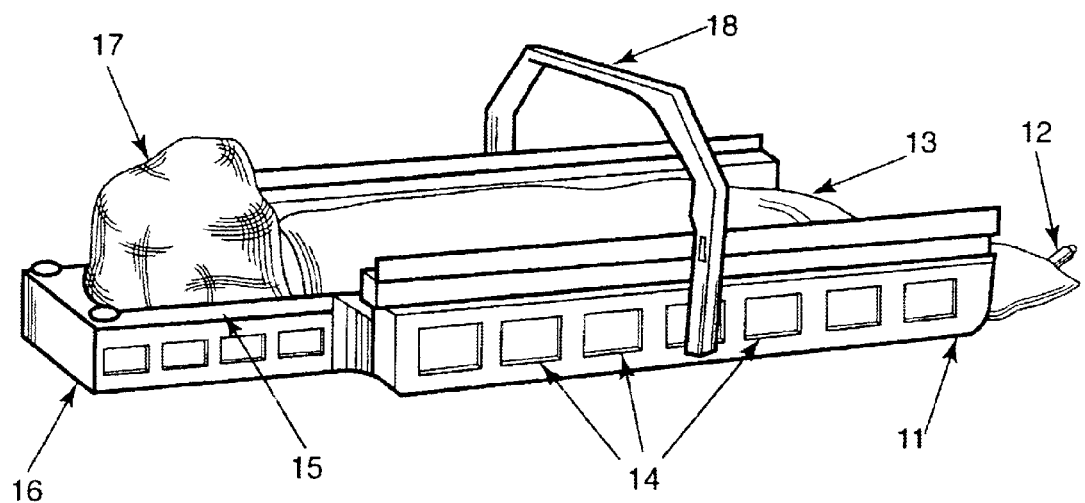
FIG. 7 is a perspective view of the system of the invention with the vacuum mold and the thermoplastic face mold in place.
Figure 8:
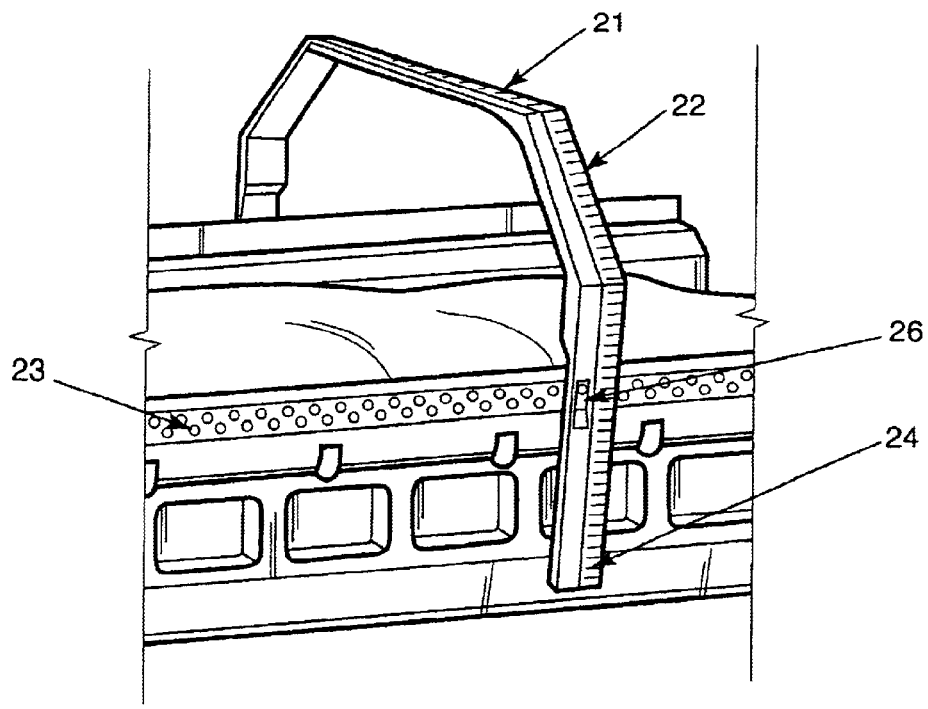
FIG. 8 is a close-up perspective view of the system of the invention showing the movable arc with x and y-axis scales; the movable arc can be locked in selected positions along the z-axis and can hold various biopsy and other localization modules.
Figure 9:
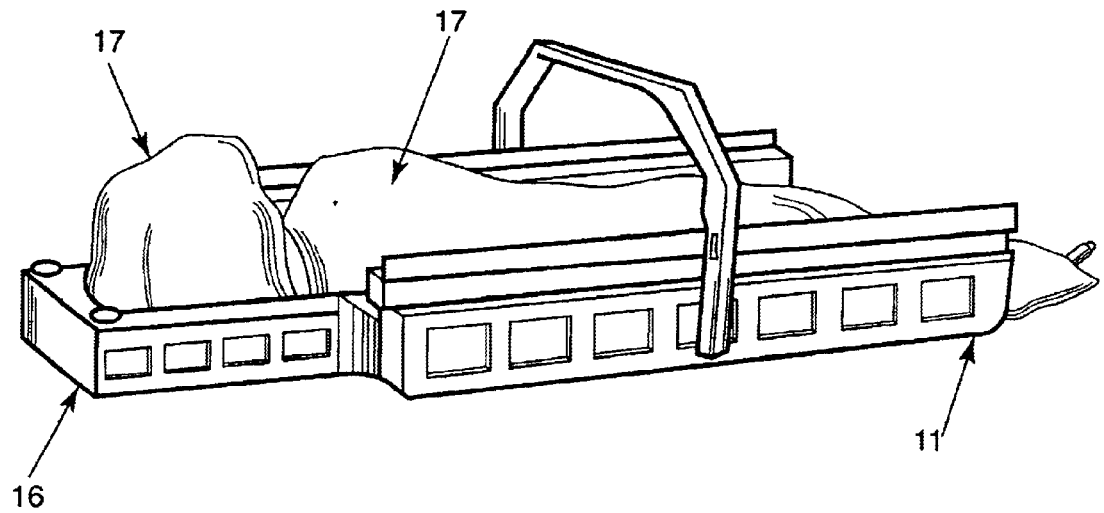
FIG. 9 is a side perspective view of the system of the invention with the vacuum mold and the thermoplastic face mold and anterior body mold in place.

The fiducial pattern as seen from the end (an axial scan slice view) is shown in FIGS. 5–6. The x and y-coordinates are determined directly from the image data according to known widths and heights of fiducial relations of the invention.

The frame of the invention is designed to be imaged by the use of axial images taken in serial sections along the z-axis (longitudinal) of the system. Fiducials seen on axial scan images can be localized by placing a cursor over the center of each fiducial and obtaining the x-y display screen coordinates. This screen coordinate data is used to calculate the z-axis position of a target and its x and y coordinates in stereotactic frame space according to the invention. Note that for every incremental change in the value of x along fiducial 5, the change of the z value is 12.5 x. Localization of a z position solely derived by the use of the slope of fiducial 5 is, therefore, not sufficiently accurate to precisely define a position for incremental changes of x. Resolution of a position along z can be improved by the use of a resolver system which increases the precision of localization along z with changes in the value of x. This has been achieved by the use of two repetitive trigonometric waveform fiducials, phase linked, by the offset difference $\pi/2$, and comprising a sine and cosine wave fiducial pattern each with an amplitude of 40 mm and a phase length (period) of 250 mm. In this arrangement the maximal slope angle of each phase is 45° and there are a series of repetitive waveforms with a total of 4.5 phases (periods) forming the 1125 mm preferred length of the frame of the invention. The use of the resolver system of at least two offset fiducials improves the positional resolution along the z-axis for each incremental change of x from a factor of 12.5 x to 1 x because the intersection of the x-axis when crossing one fiducial near the peak of the waveform where the phase angle is at or near 90 degrees, will cross the other fiducial axis at 45 degrees. That is, for every incremental change along x, z changes by the same value ($\Delta z=\Delta x$). The sine/cosine waveforms have an offset relationship to each other such that lines passing through nodal points of each waveform form a right angle triangle with its base at the origin of the frame and the sine wave along the hypotenuse.

For purposes of the specification and claims, an "imaging resolver" is an array of imaging fiducials arranged in a mathematically predictable pattern that permits the calculation of finer incremental resolution along another fiducial pattern, such fiducial patterns being used to define a multi-dimensional data set and portions thereof. An imaging resolver can be used to more precisely locate positions in a three-dimensional volumetric data set (stereotactic space) or a two-dimensional data set such as obtained from imaging with scanning devices such as CT, MRI, and like imaging systems used to define or sample a three-dimensional data set. An imaging resolver is preferably positioned in an instrument about a patient's body and multi-dimensional image data sets can represent portions of the patient's body. The imaging resolver of the invention comprises a continuous array of coupled fiducials, avoiding the difficulties and inaccuracies inherent in the use of phantom simulators (Hamilton, et al., 1995) and in non-continuous, saltatorial, or serially recurrent fiducial patterns such as found in prior art devices like that defined by Onik, et al., (U.S. Pat. No. 4,583,538) and Lax, et al., 1994.

Figure 11:
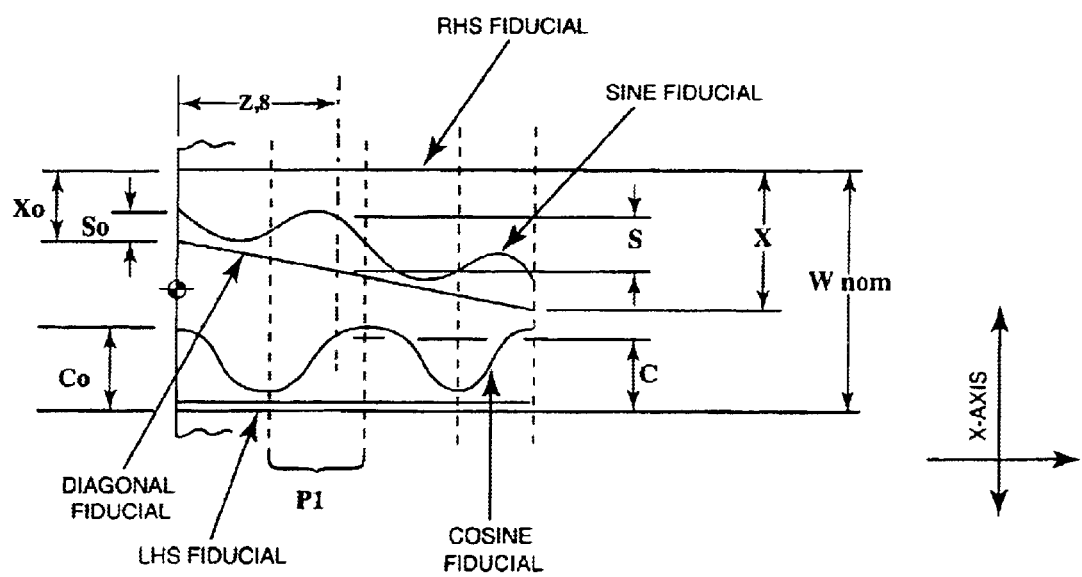
FIG. 11 is an illustration delineating decoding according to the resolver of the invention.
Figure 12A:
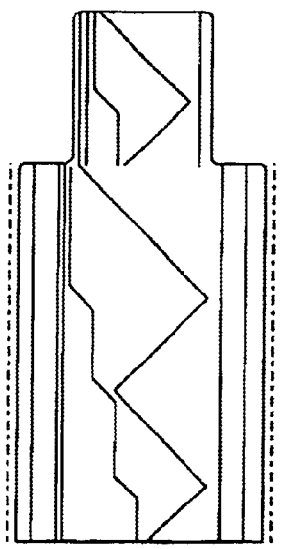
FIGS. 12(a)–12(e) illustrate alternative embodiments of the fiducial array (geometry) of the invention.
Figure 12B:
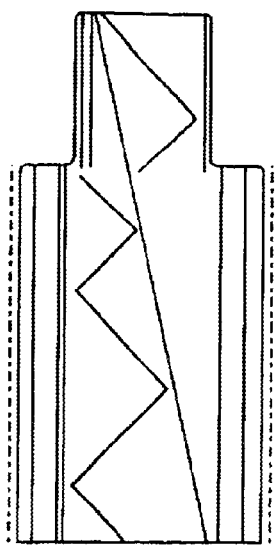
Figure 12C:
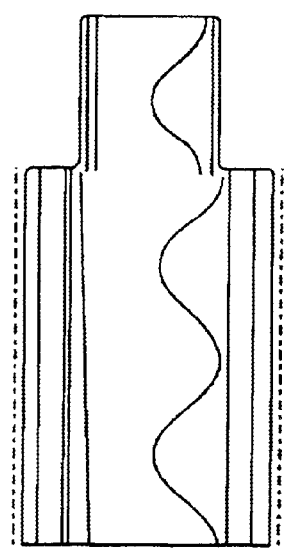
Figure 12D:
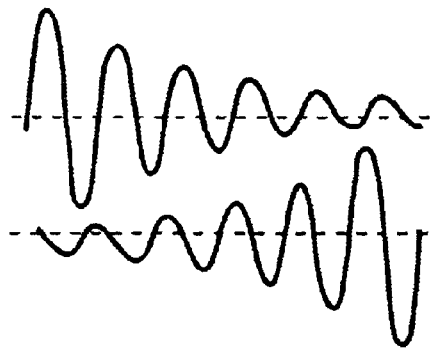
Figure 12E:
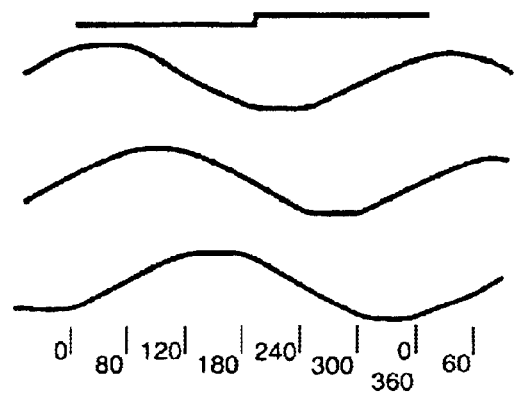

Referring to FIG. 11, illustrating the preferred resolver decoding method of the invention, all fiducials referred to are preferably on the anterior surface of the base of the frame of the invention. The term "angle" ($\Theta$) refers to a quantity which varies linearly over the length of the device, from a value of zero at Z=0 mm to a value of $9\pi$ at Z=1125 mm. The sine and cosine of this quantity are represented by the sine and cosine fiducials, respectively. RHS refers to the Right-Hand Side of the frame of the invention, and LHS refers to the Left-Hand Side. CRT refers to a Cathode Ray Tube (refers to measurements made on the CRT screen and expressed in pixel units.) The constants shown are:

X0=100 [nominal distance between RHS and diagonal fiducials at Z=0 (mm)]

S0=50 [nominal distance between diagonal and sine fiducials at Z=0 (mm)]

C0=60 [nominal distance between LHS and cosine fiducials at Z=0 (mm)]

Wnom=300 [nominal distance between LHS and RHS fiducials (mm)]

Slope=0.08 [nominal slope of diagonal fiducial (mm/mm)]

Pitch=250 [nominal pitch of [sinusoids]sinusoids (mm/cycle)]

Amp=40 [nominal amplitude of sinusoids (mm)]

Thetaslope=Slope*Pitch/($2\pi$) [slope of diagonal fiducial versus angle (mm/radian)]

Measurements referred to are:

Wpix: distance between LHS and RHS fiducials (pixels)

Xpix: distance from RHS to diagonal fiducial (pixels)

Spix: distance between diagonal and sine fiducials (pixels)

Cpix: distance between LHS and cosine fiducials (pixels)

Calculations employed by the imaging resolver include:

The preferred required input from users of the invention will be the eight (8) fiducials from the target image, along with the target point—all in screen coordinates (x-y). There will be no requirement for the location of the origin of the screen coordinates entered. The output will be the plane of the target image and the target (or isocenter) point in stereotactic or frame coordinates (x-y-z). All stereotactic coordinates are preferably in millimeters.

Preferred capabilities of the computer software of the invention include: a) The ability to determine the Z position (superior/inferior) and/or a target point in stereotactic coordinates based on the fiducials and target point entered. The fiducials and the target point are to be entered in screen coordinates, which can have the screen origin anywhere. b) The ability to validate the user input (fiducial screen coordinates) based on the known position of the fiducials (order error, direction error, etc.) and to notify the user if any error is detected. c) The ability to detect any distortion in the frame based on the alignment of the fiducials entered, and to notify the user if any distortion is detected. Additional preferred capabilities include the ability to detect any fault, rotation and/or skew in the image based on the fiducials entered, and to notify the user if any is detected. Such detection is a determination of an error in non-orthogonality of image slices through the stereotactic body frame.

The following are possible errors that can be determined by the preferred software of the invention: User Input—Direction Error: The screen coordinates of the fiducials are to be entered in a clockwise direction, beginning with the anterior-right side of the image (anterior left side of the patient). This is extremely important for the accurate determination of the Z plane and the target point. Fiducial entry in the wrong direction would give an incorrect X (or left-right) stereotactic coordinate. Because the screen origin may differ between scanner consoles or any other imaging system used to determine the screen coordinates of the fiducials, it is not advisable for the fiducials to be re-ordered according to some preset origin. However, an incorrect entry order can be determined once the first few fiducials have been entered. Therefore, the order of fiducial entries are preferably verified by the program after user entry and prior to processing. User Input—Entry Error: Based on the known location and relationship of the fiducials to each other, any errors in screen coordinate entries made by the user can be determined. The fiducial entries are preferably verified by the program after user entry and prior to processing. Any damage, such as dropping of the component, damage to the frame, warping from prolonged exposure to heat, etc., which

```
Scale = Wnom/Wpix                                [scaling CRT to actual (mm/pixel)]
Theta_rough = (Xpix*Scal-X0)/Thetaslope          [approximate angle, based on diagonal]
Theta_rough_quad = INT(Theta_rough/( π/2)+.5)    [nearest quadrant (integer multiplier of
                                                  π/2) associated with this approximation]
Theta_rough_index = Theta_rough_quad MOD 4       [quadrant modulo 4]
IF Theta_rough_index<0 then                      [takes care of negative value that could
Theta_rough_index =Theta_rough_index +4          obtain near Z=0]
S = (S0-Spix*Scale)/Amp                          [sine]
C = (Cpix*Scale-C0)/Amp                          [cosine]
IF ABS(S)>1 THEN S = SIGN(S)                     [limits sine to allowed range]
IF ABS(C)>1 THEN C = SIGN(C)                     [limits cosine to allowed range]
SELECT Theta_rough_index
CASE 0: A = S; B = C
CASE 1: A = -C; B = S
CASE 2: A = -S; B = -C
CASE 3: A = C; B = -S                            [customizes the calculation which will
                                                  follow, in light of quadrant]
END SELECT
``` distorts the position of the fiducials, can be detected by the software based on the known locations of the fiducials in relationship to each other.

The preferred screen layout generated by the software is as follows. The first screen displays the user input required for the calculation of the target point in stereotactic frame coordinates. The buttons to the right of the screen layout (designated in bold and italics) are used for the various operations performed on the user input. The final screen displays the stereotactic coordinates (X-Y-Z) along with any errors detected in the entries made by the user.

Screen One:
Patient Name: John Doe
Patient ID: 12345
Date: XX-XX-XXXX—14:03
Diagnosis: Liver Met
Note: Enter the fiducials in a clockwise direction, beginning with the anterior-right side of the image (anterior-left side of the patient).

|  | X | Y |  |
|---|---|---|---|
| First Fiducial: | — | — | Process |
| Second Fiducial: | — | — | Configure |
| ... | ... | ... | Save |
| Eighth Fiducial: | — | — | Retrieve |
|  |  |  | Print |
|  | X | Y | Quit |
| Target: | — | — |  |

Screen Two:
Patient Name: John Doe
Patient ID: 12345
Date: XX-XX-XXXX—14:03
Diagnosis: Liver Met

| Stereotactic Coordinates: | |
|---|---|
| X: | — mm |
| Y: | — mm |
| Z: | — mm |

The preferred functions of the buttons on the display screens are as follows: 1) Process: Performs the calibration of the entered fiducial points and target point and returns the stereotactic coordinates (X-Y-Z). 2) Configure: Only used by personnel during configuration/installation of the invention. The engineer can enter the exact measurements of the system of the invention. 3) Save: Allows the user to save the current patient information, along with the fiducials and target coordinates, for retrieval at a later date, either during this session or a future session. 4) Retrieve: Allows the user to retrieve patient information, fiducials and target coordinates that were previously saved, either during this session or a previous session. 5) Print: Allows the user to print the current patient target information. 6) Quit: Exits the program, providing the user with a chance to save any current patient entries prior to exiting.

FIGS. 12(a)–12(e) illustrate alternative imaging resolver fiducial arrangements (geometry). The fiducials can also be arranged such that they are filled with or consist of material which will show up on both MRI and CT, as well as other imaging methods. For example, a polyamide or similar material may be employed configured with carbon, hydrogen, and water such that fiducials filled with this material are visible on different scanners, the material being housed in teflon or similar tubing. Sealed teflon tubing may likewise be used containing microfilaments of glass (silicon) fibers and a weak copper sulfate solution. Other mixtures or compounds may be employed to achieve similar results, as understood by one of ordinary skill in the art.

Figure 13:
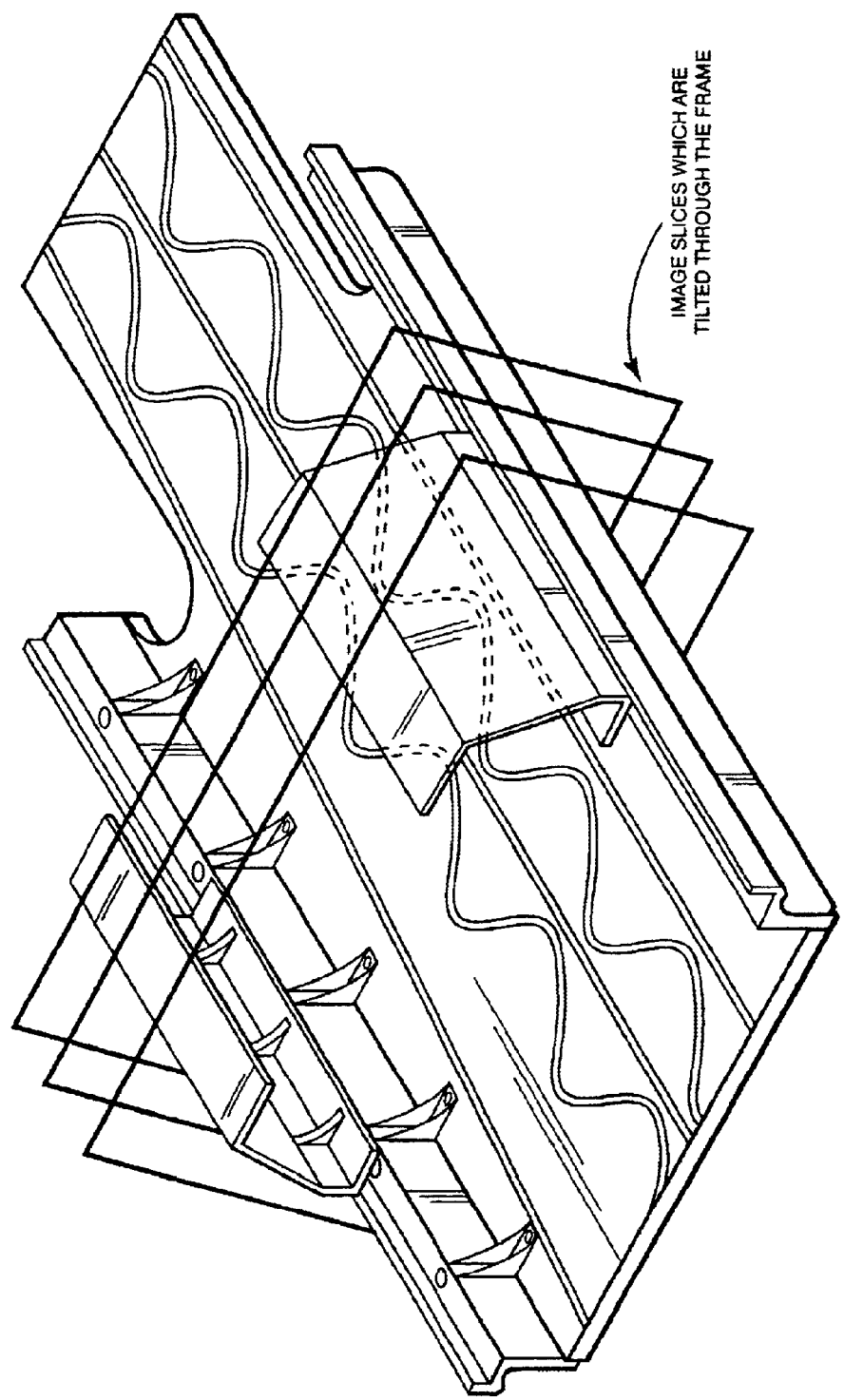
FIG. 13 is an illustration of volume image data with non-orthogonal image planes.
Figure 14A:
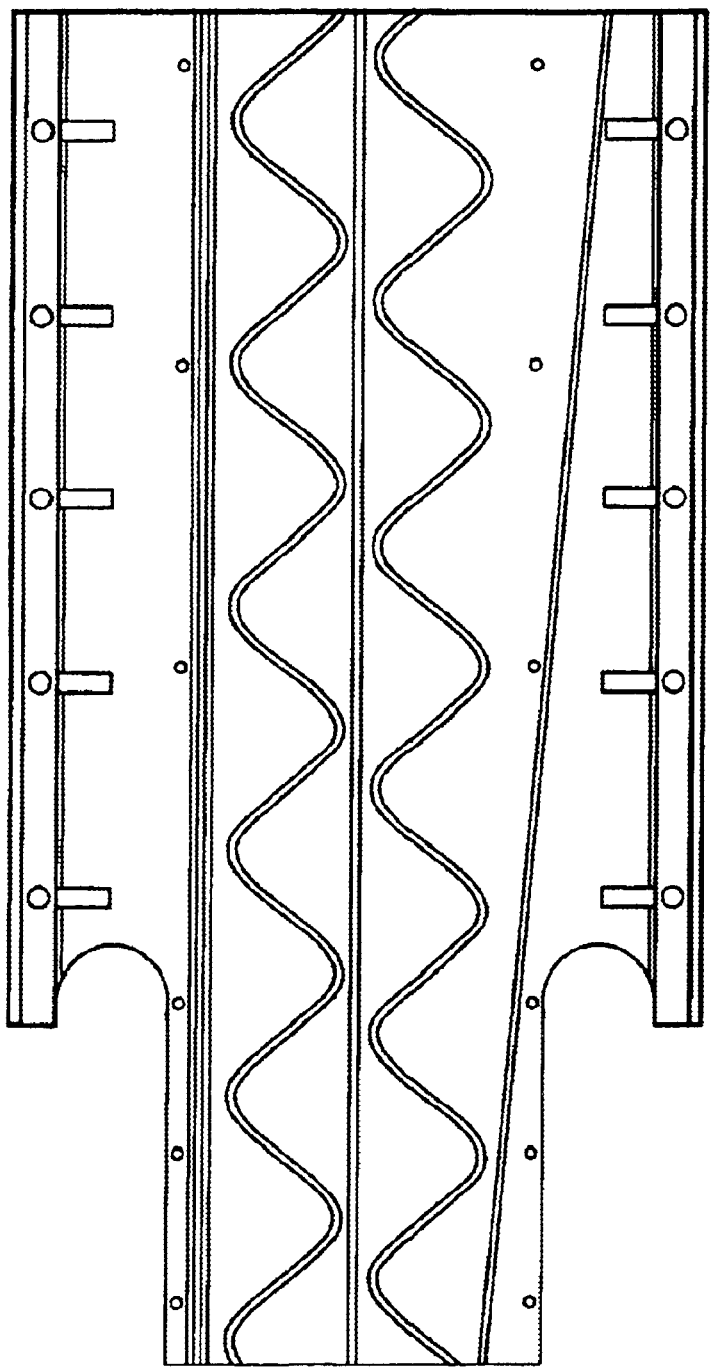
FIGS. 14(a) and (b) illustrate alternative embodiments of the fiducial array (geometry) of the invention, which allows for improved localization with non-orthogonal volume imaging.
Figure 14B:
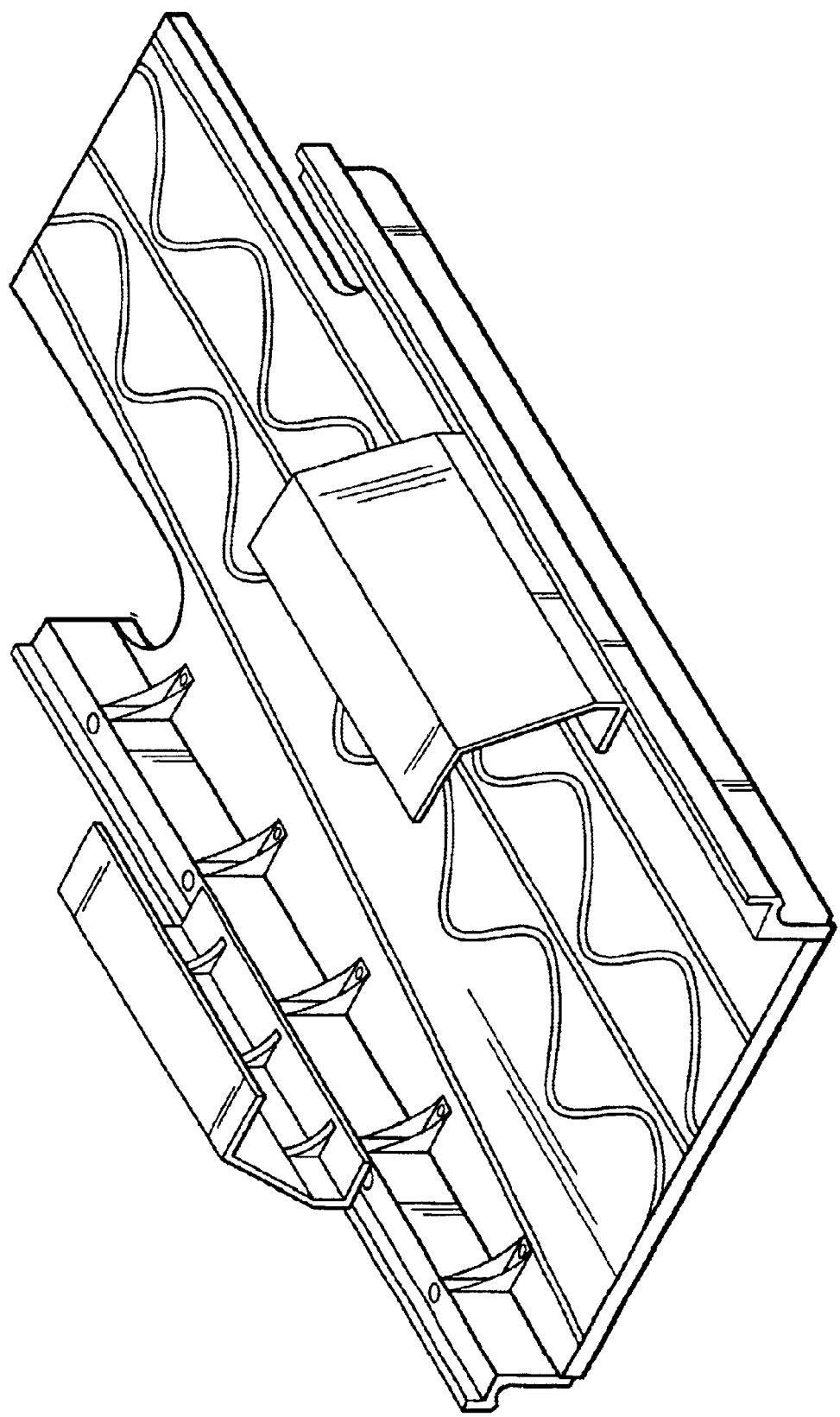

Although the frame of the preferred embodiment of the invention is designed to be imaged by the use of orthogonal axial images taken in serial sections along the z-axis (longitudinal axis) of the system, this may not be easily achieved in some clinical settings. Therefore, alternatively, in another embodiment such orthogonal alignment of the body frame within the scanner is not required. Stereotactic localization can be achieved in such cases by volume image data calculations in which a series of (at least two) parallel image slices through the fiducial array of the system are used to determine the precise geometric orientation of the image slices within the frame (FIGS. 13 and 14). In this embodiment, parallel equally spaced serial image slices are taken through the body frame in which each image slice includes the fiducial array of the frame. Additions to the steps of alignment and localization of the preferred embodiment can be employed to calculate or determine the orientation of a volume image series of individual image slices through the stereotactic body frame, so as to more precisely calculate stereotactic coordinates (pixel or voxel) in the stereotactic space regardless of any tilt rotation or skew angulation of an image slice from the true orthogonal position. Such additions include the following (and equivalents):

a) A volume image series of equally spaced parallel image slices having a known, but preferably square image matrix (e.g., 512×512), is obtained through the body frame.

b) Such image data contains information about the size in millimeters of a spatial pixel (or voxel) in the image matrix based on commonly available image scanning parameters, e.g., image field of view (FOV) and image matrix size.

c) Given a series of grayscale scanner images of a known matrix configuration (for example, 512×512×8 bits) which cut through the body frame having a known positional array of parallel fiducials defining a stereotactic spatial volume, any orientation of an image slice through the parallel fiducial array can be determined by the use of x, y screen coordinates of the fiducials appearing on the displayed images. Any delta movements of screen coordinate positions of such fiducials between sequential parallel slices will provide information to calculate the tilt, rotation or skew orientation of a slice through the body frame. Classical Euclidean or vector geometry related to parallel planes intersecting parallel lines, as well as matrix geometry, can be used to make such calculations and transformations to determine stereotactic coordinates within the body frame.

d) The resultant volume determination consists of a three dimensional volume data set having a three dimensional fiducial array in the volume data set which conforms to that of the ideal body frame.

e) Error analysis of the resultant fiducial system of the frame defined by the volume data set using the method of least squares for fitting fiducial line segments is used to determine the accuracy of the alignment and localization. Non-optimal data is rejected.

f) Alternatively, a more complex three-dimensional optimization algorithm can be employed such as previously discussed in U.S. Pat. No. 5,205,289. This algorithm is based on the concept of mathematical functional optimization using constrained multi-dimensional nonlinear optimization techniques. The word "optimization" means the rigorous use of algorithmic steps, implemented as computer code, to search for and find a mathematically defined local minimum (or maximum) or given objective function. An objective function can take many forms (e.g., calculated stress in a structural member, aerodynamic loading on a wing, a calculated dose of cell irradiation, or fitting a volume of images to a known model), but is simply a chosen measure of the desired behavior of the object, system, or process. The term "constrained optimizations" then refers to the optimization process, as explained above, being conducted within certain allowable limits or constraints. For example, in automotive engineering, a desired design objective may be to design a car frame of minimal weight. If no constraints were put on this design problem, the minimal weight of the car frame would not be able to withstand the encountered loads during operation and may not even be manufacturable. Therefore, constraints are put on the design problem that require the car frame to support certain loads under various conditions and to ensure that the final design will be manufacturable given current technology. Typically, "real world" design problems are constrained by certain necessary performance criteria. Modeling the physical behavior or real worlds objects, systems, and processes requires the use of complex nonlinear mathematical equations formed from available variables and incorporated within the computer code. Therefore, using the definitions provided in this paragraph, the term "constrained multidimensional nonlinear optimization" is defined.

Such algorithms as discussed above were designed to replace the traditional "hunt and peck" process with efficient, non-random techniques for gleaning information from the computer model in the form of slopes and curvature of the objective function "hyper-surface" (a surface with three or more variables). When coupled in this manner, the algorithms take the place of the user and autonomously search and find the optimal combination of variables to maximize or minimize a desired objective, in this case, the fit of the volume image data set to the shape of the stereotactic body frame as defined by the fiducial arrays.

Two robust and efficient nonlinear optimization algorithms available in the art are the Generalized Reduced Gradiant (GRG) algorithm and the Sequential Quadratic Programming (SQP) algorithm.

The present invention uniquely applies these numerical optimization techniques to help improve the process of fitting/aligning the volume image data set with the space defined by the body frame. By incorporating numerical optimization algorithms into the existing framework, the stereotactic alignment and localization process becomes virtually automatic and produces better localization under non-idealized imaging techniques than current techniques and in less time.

g) Once the tilt, rotation, and skew orientation of an image series through the body frame is determined, reformats of the image data can be obtained using a volume image computer system such as that described in U.S. Pat. Nos. 5,398,684, 5,099,846 or other such volume imaging systems.

Other stereotactic localization devices or systems, such as infrared, ultrasound, and electromagnetic 3-D localization devices can be attached to or be used in conjunction with the body frame to aid or enhance localization and positioning of the device. Other devices and systems emitting and/or receiving beams such as laser beams, x-ray beams, heavy particle beams, anti-matter beams, proton beams, gamma beams, ultrasonic beams, infrared beams, nuclear rays, other beams and rays, and the like, can also be attached to or used in conjunction with the body frame of the invention to allow for alternative methods of beam therapy or function as component modules for treatment or localization. The arc carriage can be used to hold surgical probes, electrodes, and beam localization and delivery systems, for example, those disclosed in U.S. Pat. Nos. 5,143,076, 5,176,689, and 5,354,314. The frame length can be extended to include the entire body, from head to toe, and additional quality assurance markers at regularly spaced intervals can be added to the system.

To summarize, the invention was developed to meet the fundamental requirements of body immobilization and stereotactic localization in a non-invasive manner. The invention is capable of immobilizing the head and neck as well as the thoracic, abdomen, and pelvis, with a fiducial localizer system that is continuous from head to pelvis and allows accurate and continuous stereotactic imaging and localization throughout the entire upper body. The advantages of the invention are increased accuracy, reliability, and whole body localization. Immobilization is achieved by the use of a vacuum mold system or polyurethane foam mold for posterior (the part of the body nearest the frame base) areas and a thermoplastic body mold to cover large body surfaces in the ventral or anterior plane. The method of combined anterior and posterior form fitting custom molded immobilization, which cover wide surface areas of the body, improves immobilization and repositioning as well as minimizing diaphragmatic movements. The vacuum or foam molds and the thermoplastic molds can be stored and reused for each patent in a fractionation treatment regimen.

Although the invention has been described in detail with particular reference to these preferred embodiments, other embodiments can achieve the same results. Variations and modifications of the present invention will be obvious to those skilled in the art and it is Intended to cover in the appended claims all such modifications and equivalents. The entire disclosures of all references, applications, patents, and publications cited above are hereby incorporated by reference.

What is claimed is:

1. A whole body stereotactic localization and immobilization system comprising:

a patient elongated support frame having a longitudinal axis including at least two fiducials, two of said at least two fiducials positioned generally parallel with the longitudinal axis, said two fiducials each comprising a repetitive trigonometric waveform, the position of the first one of said two fiducials being longitudinally offset from the position of the second one of said two fiducials; and a body immobilizing device for maintaining the patient's body in fixed relationship to the fiducials at least during imaging, of said two fiducials having trigonometric waveforms, one of said waveforms is sinusoidal and the second is cosinusoidal.

2. The whole body stereotactic localization and immobilization system of claim 1 wherein said trigonometric waveform first fiducial is a sine wave.

3. The whole body stereotactic localization and immobilization system of claim 1 wherein said trigonometric waveform second fiducial is a cosine wave.

4. The whole body stereotactic localization and immobilization system of claim 1 additionally including a longitudinally slidable carriage.

5. The whole body stereotactic localization and immobilization system of claim 1 wherein the position of the sine and cosine fiducials are transversely apart.

6. The whole body stereotactic localization and immobilization system of claim 5 wherein the position of the sine and cosine fiducials are longitudinally offset and mathematically linked by a $\pi/2$ relationship.

7. The whole body stereotactic localization and immobilization system of claim 5 wherein a fourth of said at least two fiducials is a straight line parallel to the longitudinal axis of said frame and not intersecting said trigonometric waveform fiducials.

8. The whole body stereotactic localization and immobilization system of claim 7 wherein a fifth of said at least two fiducials is a straight line.

9. The whole body stereotactic localization and immobilization system of claim 8, herein said fourth and fifth of said at least two fiducials are parallel and positioned relative to said patient elongated frame so as to lie adjacent and generally parallel to the left and right sides of the patient.

10. The whole body stereotactic localization and immobilization system of claim 9 wherein said third fiducial does not intersect said fourth and fifth parallel straight line fiducials within the confines of said patient elongated frame.

11. The whole body stereotactic localization and immobilization system of claim 10, wherein said third fiducial does not intersect the two trigonometric waveform fiducials within the confines of said patient elongated frame.

12. The whole body stereotactic localization and immobilization system of claim 11 wherein a sixth of said at least two fiducials is a straight line parallel to the longitudinal axis of said frame and adjacent one or the other of said left and right straight line fiducials so as to effect an error protection.

13. The whole body stereotactic localization and immobilization system of claim 12 wherein said first and second trigonometric waveform fiducials having varying amplitude.

14. The whole body stereotactic localization and immobilization system of claim 1 wherein a third of said at least two fiducials is a straight line non-parallel to said first longitudinal axis of said frame.

15. The whole body stereotactic localization and immobilization system of claim 1 wherein said frame need not be orthogonally aligned within a scanning device in order to permit precise stereotactic localization in images taken by the scanning device.

16. The whole body stereotactic localization and immobilization system of claim 1 additionally comprising quality assurance fiducials placed at predetermined positions along an axis of said frame.

17. The whole body stereotactic localization and immobilization system of claim 1 wherein said frame includes an arc carriage.

18. The whole body stereotactic localization and immobilization system of claim 17 wherein said arc carriage includes means for holding surgical probes, electrodes, or beam localization and delivery systems.

19. A whole body stereotactic localization and immobilization system comprising:
a patient elongated support frame including an imaging resolver having at least two fiducials each of which has a repetitive trigonometric waveform, one of said repetitive waveform fiducials offset from a second repetitive waveform fiducial, of said two fiducials having trigonometric waveforms, one of said waveforms is sinusoidal and the second is cosinusoidal; and
means for temporarily immobilizing the patient's body in relation to the imaging resolver.

20. The whole body stereotactic localization and immobilization system of claim 19 additionally including means for mathematically calculating stereotactic coordinates.

21. A method for stereotactic localization of a portion of a human body comprising:
placing the patient's human body including a lesion on a support frame;
temporarily immobilizing the patient's body during imaging by a scanning device such as computed tomography or magnetic resonance imaging;
providing a fiducial pattern on said frame for creating markers on the patient image to create a reference system;
configuring the fiducial pattern so as to include at least two fiducials each of said fiducials having a repetitive trigonometric waveform one of said repetitive waveform fiducials offset from a second repetitive waveform fiducials, of said two fiducials having trigonometric waveforms, one of said waveforms is sinusoidal and the second is cosinusoidal;
providing a computer system for displaying said images, including said markers, and a software program for utilizing said fiducial markers for accurate stereotactic positioning information;
creating a radiation therapy plan for treatment of a lesion the position of which is determined based on the images and computer program;
immobilizing the patient's body in a radiation therapy delivery device; and
delivering radiation therapy to the applicable portion of the patient's body so as to treat the lesion.

\* \* \* \* \*